May 13, 1958 O. R. BRISTOW Plant Pat. 1,707
AZALEA PLANT
Filed July 30, 1957
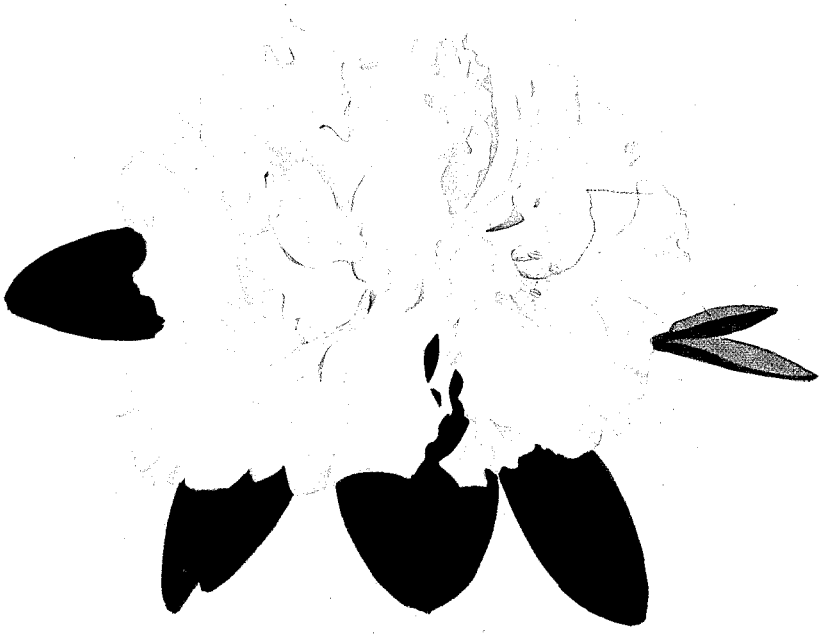
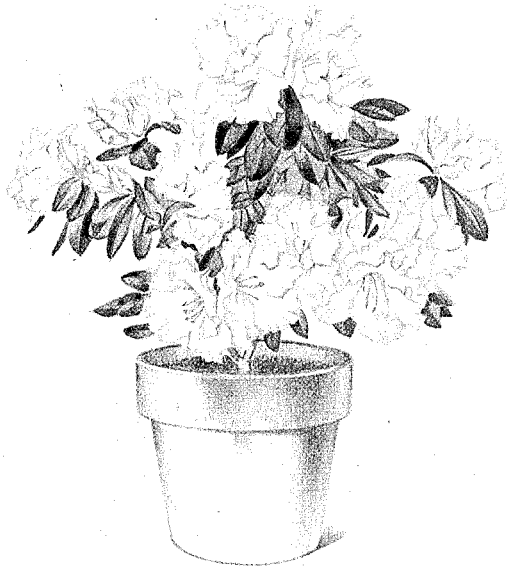
OWEN R. BRISTOW
INVENTOR.
BY Orville R. Seidner
AGENT United States Patent Office Plant Pat. 1,707
Patented May 13, 1958

1,707

AZALEA PLANT

Owen R. Bristow, San Bernardino, Calif., assignor to Mossholder Nursery, Orange County, Calif.

Application July 30, 1957, Serial No. 675,237

1 Claim. (Cl. 47—60)

This invention relates to a distinct and new variety of azalea plant reproduced as a result of deliberate experiments in hybridization carried out at my nursery in San Bernardino, California, the plant being derived from a cross-breeding of unpatented plants numbered 109B and 42 in my breeding records. This particular plant has been given the number 11A for identification purposes.

The cross-breeding resulting in plant 11A was accomplished as follows: cross-fertilization of the pistils by pollen of plants 109B and 42 was done, after which the resulting seed pods on the two plants were gathered and all seeds subsequently sown at the same time. The seeds from the pods of the two plants were inadvertently mingled, hence the sex parentage as between plants 109B and 42 is unknown for the present plant 11A. It will be noted that both plants 109B and 42 were used as males and females and pods from both of them were gathered and sown, the present plant 11A being a seedling result of the sowing. Seedling plant 11A was thereafter transplanted at my nursery in San Bernardino, California, where asexual reproduction by the known method of removing cuttings from the mature plant and potting them was accomplished by me.

A particularly distinguishing characteristic of this distinct and new variety of azalea is the growing habit and form of the plant. It is exceptional as a late bloomer, and unusual in its compact, symmetrical form. This characteristic, together with its very dark green and glossy foliage, combines with the unusually different color arrangement on the flowers to make it an outstanding Easter or Mothers Day variety.

The flowers themselves have an exceptionally distinct characteristic variation in the intensity of their pink coloring which, with an irregular white mottling, effect an inconsistent but very striking color arrangement on each individual plant.

Additionally, a further distinctiveness resides in the form of the ruffled, large opening flowers. They are seen to bloom as a large hose-in-hose to a large hose-in-hose semi-double flower.

Another distinguishing feature of the plant is that it can be grown successfully with little or no pinching into a bushy symmetrical plant, which further contributes materially to its commercial value.

Asexual reproduction by cuttings of this distinct and new variety of azalea indicates the foregoing characteristics, as well as further distinguishing characteristics brought forth in the description below, are permanently fixed, and the accompanying illustration of a forced cutting plant in bloom shows the plant, foliage, and flower as near as may be represented.

The following is a detailed specification of the plant, its foliage, and the flower, reference being had to the British Horticultural Chart of the British Colour Council for color identification.

*Plant*

Form of plant: Exceptionally bushy and compact; symmetrical. Even if plant is not regularly pinched or pruned, it will grow compactly and bushy.

Growth habit: A fast grower.

Rooting: Roots well; strong grower on its own roots; very vigorous.

Blooming habit: Prolific.

Blooming season: Later than almost all other related azaleas; late April or early May.

Suitability for forcing: Exceptional as a late forcing variety.

*Foliage*

Size: Mature leaves average 2" in length by ¾" wide.

Quantity: Abundant.

Color: New foliage—upper side, light green, glossy; under side, light green, flat. Old foliage—upper side, exceptionally dark green, glossy; under side, light green, semi-glossy.

Shape: Oval shaped; very slightly pointed.

Texture: Normal.

Edge or margin: Smooth.

Ribs and veins: More prominent than average.

Aspect: Large deep green, glossy foliage; abundant.

*Flower*

Size: Average 3" to 3½" across.

Flowers born: Average 3 on a stem; sometimes 2, occasionally 4.

Quantity of bloom: Abundant.

Continuity: Flowers hold well.

Petalage:

*Size.*—Average 1½" wide; 2" to 2¼" long on inside hose or cycles of petals. Average 1¼" wide by 1½" long on outside hose or cycle of petals.

*Number of petals under normal conditions.*—5 on inside cycle; 5 on outside cylce.

*Color of bud.*—First showing is mottled pink, Plate #23/1, and off-white, Plate #603/$_3$. Prior to opening bud is mottled pink, Plate #23/2, and white.

*Color of open flower.*—Basic color of flower is pink. Center of upper half of flower is white with a slightly greenish-yellow tint, Plate #523. Pink flower is faintly blotched with white (some flowers with more blotching than others), usually near outside edge of petals.

*Texture.*—Smooth.

Appearance: Hose-in-hose flower, usually with a slight separation between hoses or layers of petals. Inside hose is moderately ruffled at edge of flower; outside hose or layer slightly smaller than inside and not as ruffled. Individual petals of outside hose asymmetrically shaped, varying from a few near perfect to various interesting mutations. A single petal on outside usually appears to be two or three (occasionally more) petals because of its irregular edge. Some of flowers are hose-in-hose semi-double due to petaloids on some of stamens.

Shape: A ruffled hose-in-hose wide opening flower.

Arrangement: Average 3, sometimes 2 and sometimes 4, on each stem.

Persistence: Sets buds regularly every year.

*Reproductive organs*

Stamens: Normal; 7 to 9.

*Anther.*—Normal, light brown.

*Filament.*—Pink.

Pollen: Yellow; small amount of pollen.

Pistil: Normal.

*Style.*—Pink.

*Stigma.*—Yellow with pink veins.

Ovary: Normal; slightly larger than average.

Having illustrated and described the invention or discovery, what is claimed as new and patentable is:

A distinct and new variety of azalea plant, substantially as illustrated and described hereinabove, and characterized generally by its compact, bushy, symmetrical plant aspect with very dark green, glossy foliage, and particularly characterized by the exceptionally different color markings on the hose-in-hose and hose-in-hose semi-double ruffled flowers as seen to be a variation in their pink coloring with irregular white mottling.

No references cited